United States Patent [19]

Morris et al.

[11] Patent Number: 5,473,812
[45] Date of Patent: Dec. 12, 1995

[54] METHOD OF MANUFACTURING MEDICAL ELECTRICAL LEAD HAVING A TORQUE INDICATOR

[75] Inventors: Mary M. Morris, Moundsview; John S. Germanson, Golden Valley; Michael A. Ruff, Blaine; Richard D. Sandstrom, Scandia, all of Minn.

[73] Assignee: Medtronic, Inc., Minneapolis, Minn.

[21] Appl. No.: 227,429

[22] Filed: Apr. 14, 1994

Related U.S. Application Data

[63] Continuation-in-part of Ser. No. 40,735, Jan. 19, 1993, Pat. No. 5,374,286.

[51] Int. Cl.$^6$ ............................................. H01R 43/00
[52] U.S. Cl. ............................................. 29/825; 607/127
[58] Field of Search ............................ 29/825; 264/104; 174/DIG. 8; 607/127

[56] References Cited

U.S. PATENT DOCUMENTS

| | | |
|---|---|---|
| 3,974,834 | 8/1976 | Kane . |
| 4,046,151 | 9/1977 | Rose . |
| 4,105,732 | 8/1978 | Slingluff ........................ 264/104 |
| 4,146,036 | 3/1979 | Dutcher et al. . |
| 4,497,239 | 5/1984 | Krütten . |
| 4,570,642 | 2/1986 | Kane et al. . |
| 4,572,605 | 2/1986 | Hess . |
| 4,667,686 | 5/1987 | Peers-Travarton . |
| 4,771,777 | 9/1988 | Horzewski et al. . |
| 5,056,517 | 10/1991 | Fenici . |
| 5,143,090 | 9/1992 | Dutcher et al. . |
| 5,217,028 | 6/1993 | Dutcher et al. . |

FOREIGN PATENT DOCUMENTS 2504394   10/1982   France .

*Primary Examiner*—Carl J. Arbes
*Attorney, Agent, or Firm*—Michael J. Jaro; Harold R. Patton

[57] ABSTRACT

A medical electrical lead and method of manufacturing such a lead for use in cardiac pacing, the lead having a distal end having an active fixation device such as a helix electrode (46) having a distal end and a proximal end, the tissue securing means extending from the lead body distal end, an electrical conductor (15) extending between the proximal and distal ends of the lead, and a longitudinally extending torque indicator (35 or 36) affixed to the lead body (10) proximal to the tissue securing means, the torque indicator (35 or 36) showing rotational movement or distortion of the torque indicator (35 or 36) under fluoroscopy.

18 Claims, 9 Drawing Sheets

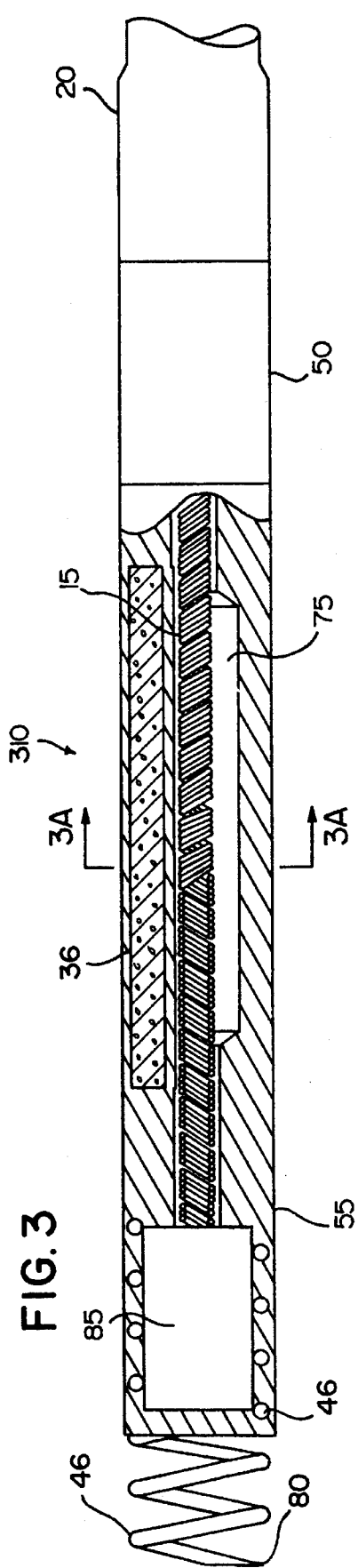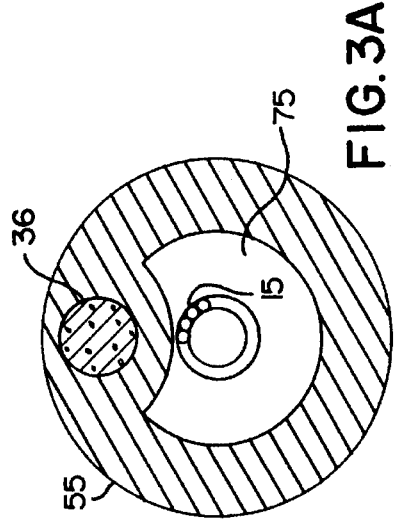

METHOD OF MANUFACTURING MEDICAL ELECTRICAL LEAD HAVING A TORQUE INDICATOR

REFERENCE TO RELATED APPLICATION

This is a continuation-in-part of a application of Morris, filed Jan. 19, 1993, entitled "TORQUE INDICATOR FOR FIXED SCREW LEADS" and having Ser. No. 08/040,735 now U.S. Pat. No. 5,374,286 issued Dec. 20, 1994.

FIELD OF THE INVENTION

The present invention relates to a medical electrical lead used to connect an organ inside a living animal body to an electrical device, and more particularly to a cardiac pacing lead used to connect an implantable pulse generator to a human heart. The present invention is also concerned with a method of manufacturing such a lead.

BACKGROUND OF THE INVENTION

There are generally two types of body-implantable leads used with cardiac pacemakers, myocardial and endocardial. Myocardial leads presently require surgery to expose the myocardial tissue to which the electrode is affixed.

Endocardial leads have an electrode or electrodes located at the distal end and are inserted in and guided through a body vessel, such as a vein, into the heart where the electrodes contact, and in some cases, are secured to the heart through the endothelial tissue lining the heart interior. Endocardial leads are divided into active and passive fixation leads. Passive fixation leads are non-penetrating leads. Tines are an example of passive fixation leads. Active fixation leads are penetrating leads. Applicant's fixed screw lead is an example of an active fixation lead.

An important feature of an endocardial lead is that of having a means of securing the electrode to the heart without dislodgement. Active fixation leads reduce dislodgements. A disadvantage of prior art leads is that it may be difficult to know when the lead has been successfully embedded in the cardiac tissue. With a fixed screw lead, for example, it may be difficult to judge how many turns are necessary to embed or remove the helix without turning the lead too many times thereby causing undue trauma to the tissue. With such leads, the physician must tactilely determine the number of rotations necessary to achieve lead fixation. Proper lead fixation is important because if the screw or helix is not fully screwed into the tissue the lead may dislodge. On the other hand if the lead is screwed too much into the tissue the tissue may be damaged, possibly injuring the patient or impairing lead performance or both.

Endocardial screw-in type leads are well known in the art. For example, the U.S. Pat. No. 4,146,036 to Dutcher et. al discloses a unipolar fixed screw lead. With such leads, the physician tactilely determines the number of rotations necessary to achieve lead fixation.

U.S. Pat. No. 4,570,642 to Kane et al discloses an endocardial, unipolar, extendable screw-in lead. With such leads, the physician observes helix extension under fluoroscopy during lead fixation.

U.S. Pat. No. 3,974,834 to Kane et. al discloses an endocardial, bipolar, screw-in lead. With such leads, the physician tactually determines the number of rotations necessary to achieve lead fixation.

U.S. Pat. No. 4,046,151 to Rose discloses an endocardial, bipolar, screw-in lead. With such leads, the physician tactually determines the number of rotations necessary to achieve lead fixation.

U.S. Pat. No. 4,572,605 to Hess, discloses a typical connector assembly for a bipolar coaxial lead. With such leads, the physician tactually determines the number of rotations necessary to achieve lead fixation.

The use of fluoroscopy to detect longitudinal motion is well known in catheter art. See, U.S. Pat. No. 4,771,777 to Horzewski et al at col. 4, lns. 17–20.

SUMMARY OF THE INVENTION

The present invention aids physicians in determining the amount of torque to apply when implanting or explanting leads. This is necessary because, due to the twistability of the lead body, the number of rotations applied at the proximal end of the lead is not always equal to the number of rotations transferred to the distal end of the lead. The present invention provides a torque indicator on or near the outer diameter of the TR (Tip-to-Ring) spacer. Specifically the torque indicator is fashioned from a radiopaque marker mounted either externally or internally to the lead body. This radiopaque marker is easily seen using a fluoroscope. The torque indicator is useful in two aspects. First, during implant, rotations of the torque indicator are easier to count than the rotations of a symmetrical radiopaque helix. Second, after the helix is imbedded in the heart tissue the torque indicator initially appears co-linear; further rotation then causes distortion of the radiopaque torque indicator strip into a spiral configuration. Distortion of the torque indicator is visible under fluoroscopy as the torque indicator no longer is co-linear to the conductor spring coil and will be visible from all views.

The above features and advantages of the present invention, as well as others, are accomplished by providing a body-implantable lead having a proximal end and a distal end, the proximal end connected to a medical device, a tissue securing means having a distal end and a proximal end, the tissue securing means extending from the lead body distal end, an electrical conductor extending between the proximal and distal ends of the lead, and a longitudinally extending torque indicator affixed to the lead body proximal to the tissue securing means, preferably the torque indicator is a radiopaque marker to thereby show rotational movement or torque distortion of the lead under fluoroscopy. The tissue securing means comprises a helix axially aligned with the lead body and is attached to the electrical conductor. The helix may also be electrically insulated from the electrical conductor with the lead body having an electrode electrically connected to the distal end of the conductor. The torque indicator comprises a flexible radiopaque marker of a cylindrical shape approximately 0.025 inches (0.0635 cm) in diameter and approximately 0.75 to 0.5 inches (1.9–1.27 cm) in length fastened to the lead body.

A lead having a torque indicator may be provided in several configurations. First a lead having a torque indicator may be provided through a lead body having a center axis, a proximal end and a distal end; means for securing the distal end of the lead to tissue, the means for securing extending from the lead body distal end; an electrical conductor extending between the proximal and distal ends of the lead body; and a radiopaque marker having a center axis, the radiopaque marker affixed to the lead body at a position so that the radiopaque marker center axis is offset from the lead body center axis.

Alternatively a lead having a torque indicator may be provided through a lead body having an outer wall, a proximal end and a distal end; an electrical conductor extending between the proximal and distal ends of the lead body; a helix attached to the distal end of the lead body, the helix axially aligned with the lead body; and a radiopaque marker affixed to the outer wall of the lead body proximal to the helix.

Still alternatively a lead having a torque indicator may be provided through a lead body having an outer wall, a proximal end and a distal end, the lead body having a first section and a second section, the first section being located near the distal end, the second section being located near the proximal end, the first section being more flexible than the second section; an electrical conductor extending between the proximal and distal ends of the lead body; a helix attached to the distal end of the lead body, the helix axially aligned with the lead body; and a radiopaque marker affixed to the first section of the lead body.

The present invention is specifically concerned with a method of manufacturing a lead having a torque indicator, and in particular a radiopaque marker positioned along the lead body. The basic method involves molding the TR spacer of the present lead having a torque indicator therewith. The preferred method of molding has essentially three stages: molding the radiopaque marker and the TR spacer sub assembly; molding the helix to the TR spacer sub assembly to create the TR spacer and, finally, assembling the TR spacer and the various lead components to create the final lead. The first stage of the preferred method may be accomplished in two fashions, through a cold transfer molding process or through a backfill process. An alternative to the preferred method is also disclosed. This method involves externally applying a radiopaque marker to the lead body, preferably proximate the distal portion.

Other features, advantages and objects of the lead and method of manufacture of present invention will hereinafter become more fully apparent from the following description of the drawings, which illustrate the invention.

BRIEF DESCRIPTION OF THE DRAWINGS

FIG. 3 shows a view of an internal torque indicator inside elevation partly in longitudinal section which is an alternative embodiment of the distal end portion of the lead of FIG. 2;

FIG. 3a shows a view of the cross-section of FIG. 3 along the lines 3—3;

DETAILED DESCRIPTION OF THE PREFERRED EMBODIMENTS

The following specification will first briefly describe the procedure for implanting a lead then describe the major lead components and finally describe a method of manufacturing such a lead. The lead components are the electrode, spring coil conductor, torque indicator and its typical methods of manufacturing, tissue securing means such as the helix, outer tubing, TR (tip to ring) spacer, anode ring and sealing rings. For purposes of this application, the invention will be described for use as an endocardial pacing and sensing lead for connecting an artificial cardiac pacemaker to cardiac tissue. Nevertheless, the lead could as well be applied to other types of body stimulating systems. Although applicant's invention represents an endocardial type lead, the invention may apply to myocardial leads in the future, as for example with endoscopic equipment. In that particular usage, the present invention may feature a torque indicator which may be either radiopaque or visible under detectable light or both. In short, the scope of the present invention relates simply to a medical electrical lead which indicates the presence of torque in a portion of the lead once the helix has been screwed into position.

MEDICAL ELECTRICAL LEAD IMPLANTATION

Figure 1:
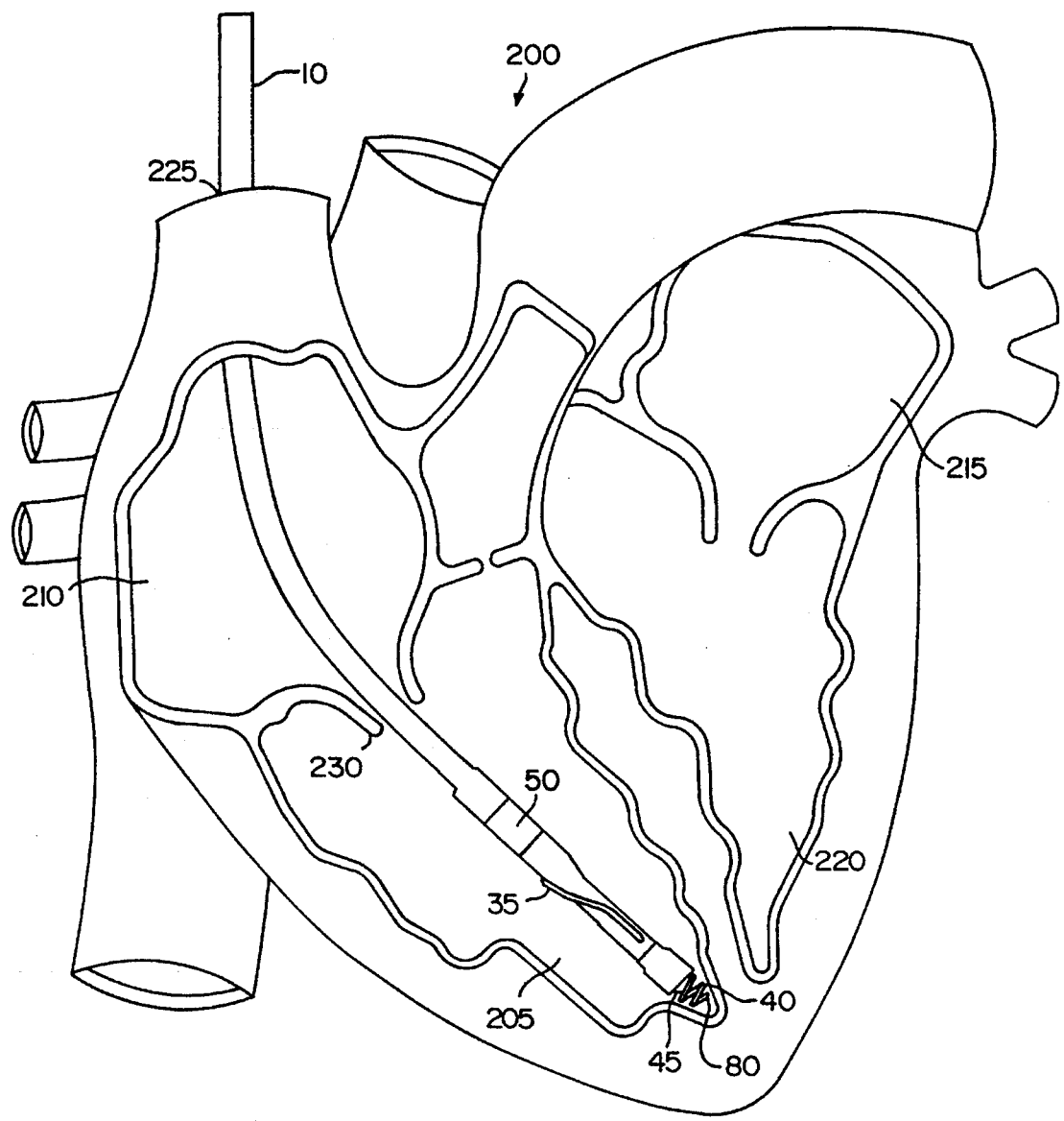
FIG. 1 shows the lead of FIG. 2 being lodged in and permanently secured to the tissue forming the apex of the right ventricle of the heart.
Figure 2:
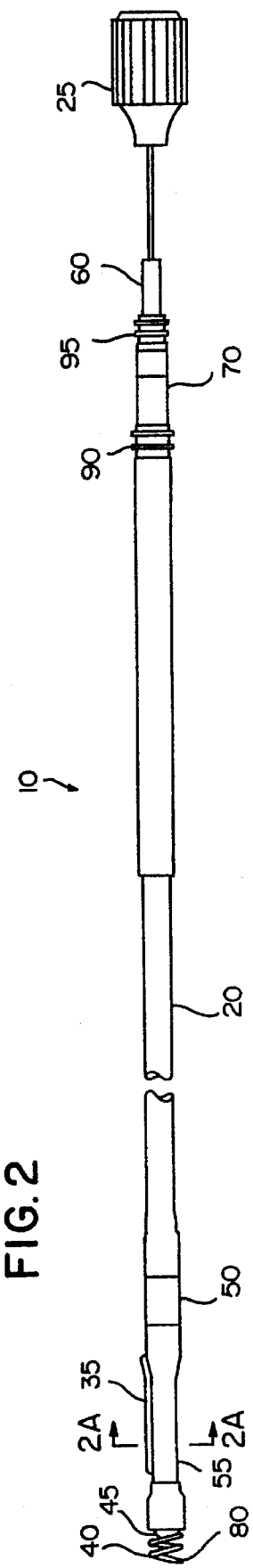
FIG. 2 shows a view of a body-implantable, endocardial fixed screw lead with an electrically inactive helix, a separate electrically active electrode and an external torque indicator.

Referring to FIG. 1, the heart 200 in cross section comprises the four chambers, namely, the right ventricle 205, the right atrium 210, the left atrium 215 and the left ventricle 220. In the placement of an endocardial lead 10, it is preferable to use a venous approach on the low pressure side of the heart. For example, the typical ventricular path as depicted in FIG. 1, would begin through a vein such as the right or left external subclavian vein, or the right or left cephalic veins, then through the superior vena cava 225, the right atrium 210, and, if desired, through the tricuspid valve 230 and to the right ventricle 205. Stylet 25 as in FIG. 2 is used to control the location of implant. It should be noted, however, that most screw-in leads are implanted in the right atrium 210, although for purposes of describing the present invention an implantation into the right ventricle 205 will be described.

After the lead 10 in FIG. 1 is passed through the tricuspid valve 230 and into the right ventricle 205, a suitable location for implant may be determined by placing the electrode 45 tip adjacent to the heart tissue and taking stimulation and/or sensing thresholds. After a suitable location has been determined, the lead 10 is rotated around stylet 25 as in FIG. 2 to screw helix 40 into the tissue at the desired stimulation site. The torque indicator 35 aids the physician in determining the proper number of rotations. After the helix 40 has been firmly affixed to the tissue, the stylet 25 is pulled proximally and removed from the lead 10.

MEDICAL ELECTRICAL LEAD HAVING A TORQUE INDICATOR

The present invention can use either a unipolar or a bipolar lead; FIGS. 1–3 represent bipolar leads. A bipolar configuration carries two electrodes and two conductors. In FIG. 2 which depicts a lead with an external torque indicator 35, the two electrodes are shown as the anode ring 50 and the electrode 45. FIG. 3 depicts an alternative embodiment of FIG. 2, with FIG. 3 having an internal torque indicator or marker 36. In FIG. 3, the two electrodes are shown as the anode ring 50 and the helix electrode 46. In both the FIG. 2 and FIG. 3 embodiments the two conductors comprise an outer spring coil 16 and an inner spring coil 15. As for example, in FIG. 3, the outer spring coil 16 is wound about and along the axis of the inner spring coil 15. The Tip-to-Ring (TR) Spacer 55 provides the electrically insulated separation between the two electrodes to permit signal sensing.

Figure 2A:
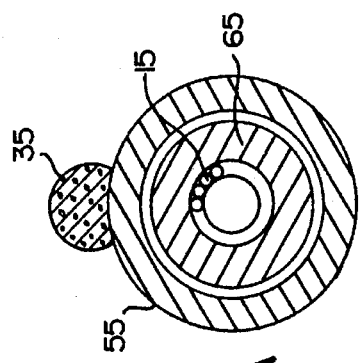
FIG. 2a shows a view of the cross-section of FIG. 2 along the lines 2—2.
Figure 3B:
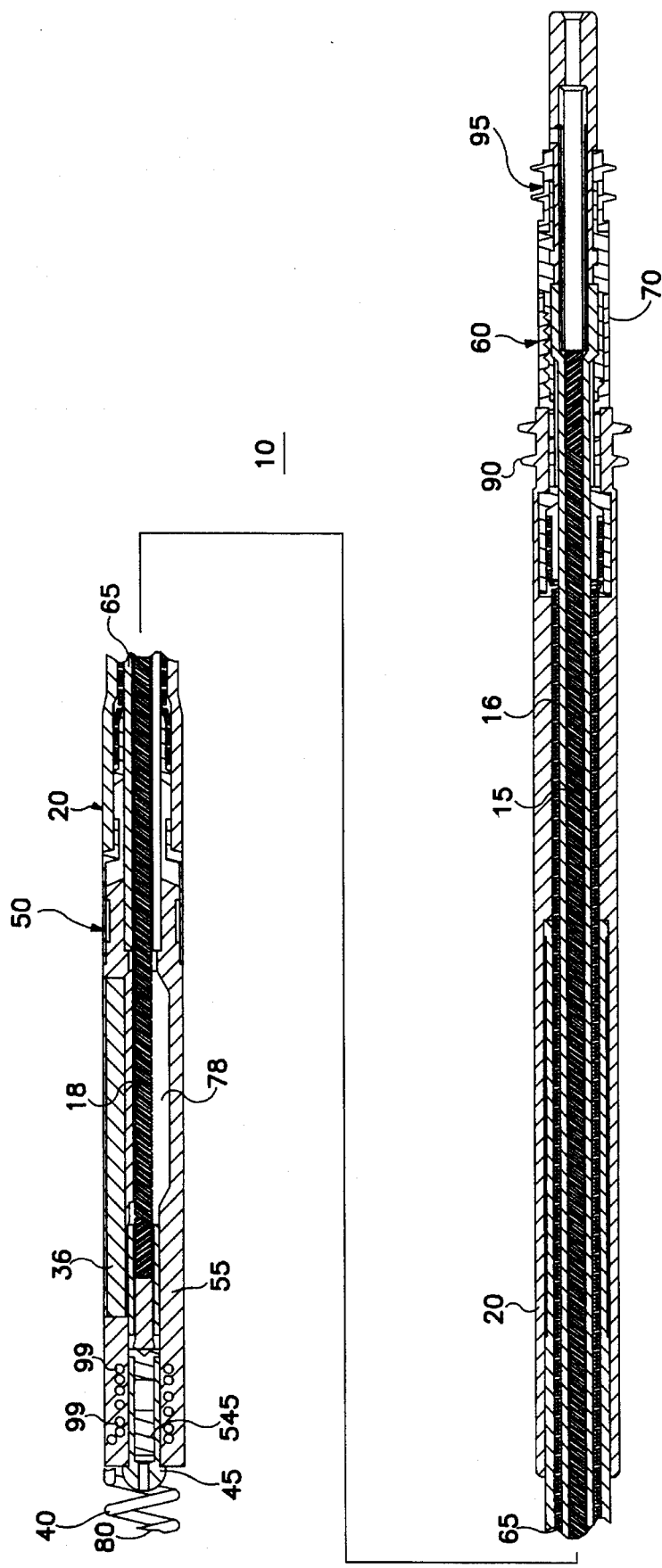
FIG. 3b shows a view of an internal torque indicator which is an alternative embodiment of the distal end portion of the lead of FIG. 3.

In a bipolar lead the two conductors may be coaxial or bi-axial coils. In the illustrated embodiments, the coils are co-axial. The conductor spring coil construction is the same in both the external torque indicator 35 embodiment seen in FIG. 2 as in the internal torque indicator 36 embodiment seen in FIG. 3. The inner and outer conductors are both spring coils and can be formed of a nickel alloy. The inner spring coil 15 distal end is connected to the helix electrode 46 as in FIG. 3a and to the electrode 45 in FIG. 2 by a variety of means, as for example, through the use of a platinum alloy crimp tube. In addition, as best seen in FIG. 3b anode ring 50 is electrically connected to outer coil 16 while electrode 45 is electrically connected to inner coil 15. Preferably electrode 45 is a porous platinized electrode as is well known in the art. The proximal end of inner spring coil 15 is connected to the pin 60. The outer spring coil distal end is connected to the anode ring 50. At the proximal end the outer spring coil is connected to the connector ring 70. The inner spring coil in the embodiments extends through the length of the lead body in a tubular insulating sheath 65 extending between the inner spring coil 15 and outer spring coil, the sheath 65 comprising a lumen as seen in FIG. 2A. The outer spring coil extends through the length of the lead 10 in a lumen of outer tubing 20 of electrically insulating material.

Both inner spring coil 15 as well as outer spring coil are formed of electrically conductive material offering low electrical resistance and resistance to corrosion by body fluids. A nickel alloy, such as MP35N, is an example of a suitable conductor material.

A lead such as 10 using a conductor coil such as inner spring coil 15 has been shown to be capable of withstanding constant, rapidly repeated flexing over a period of time which can be measured in years. The inner spring coil 15 is wound relatively tightly, although there can be a slight space between adjacent turns. The spirally coiled spring construction of the spring coil 15 also permits a substantial degree of elongation, within the elastic limits of the material, as well as distribution of flexing stresses along the conductor which otherwise might be concentrated at a particular point. Both the inner spring coil 15 and the outer tubing 20 are elastic, and this, together with the coiled construction of the inner spring coil 15, assures maximum distribution of flexing stresses. The spring coil 15 may also comprise a multi-filar redundant coil of thinner wire.

The torque indicator 35 or 36 is preferably made of biocompatible radiopaque materials such as platinum, iridium, gold or tantalum. It is more preferably made of platinum loaded silicone with a concentration of 4 grams platinum per cc of silicone adhesive. The optimal concentration of the radiopaque element is a function of the torque indicator's thickness and type of radiopaque material selected. The preferred torque indicator diameter is approximately 0.025 inches (0.0635 cm) with a length of approximately 0.75–0.5 inches (1.9–1.27 cm). As seen in the FIGS. the torque indicator 35 or 36 is preferably mounted co-linear with the lead, although not co-axial. In such a manner when the marker begins to flex due to the twisting of the lead body due to torque, as depicted in FIG. 1, the marker will flex to thereby readily indicate torque.

The tissue securing means and electrode could be combined as a unitary entity or could be separate entities. An example of a unitary entity is a fixed screw lead with the screw as the electrically active electrode 46 as in FIG. 3. FIG. 3b shows a view of an internal torque indicator which is an alternative embodiment of the distal end portion of the lead of FIG. 3. An example of separate entities is a tissue securing means consisting of an electrically inactive fixed helix 40 and a separate electrically active electrode 45 as in FIGS. 1 and 2.

The tissue securing means can take the form of a relatively rigid circular corkscrew which can be either an electrically inactive helix 40 as in FIGS. 2 or 3b or helix electrode 46 as shown in FIG. 3. This form of a helix consists of approximately two closely wound turns of platinum-iridium coil made of approximately 0.012 inch (0.0305 cm) diameter wire. These turns end in a sharpened tip 80 at a point on the inside circumference on the wire making it up. The tip readily penetrates the endocardium. The tip further penetrates the tissue with the addition of clockwise rotation of the proximal lead body. The tip extends beyond the distal end of the lead body by about 0.08 inches (0.20 cm). Preferably the root portion of helix 40, located within the lead 10 and specifically anchored within the lead body material, has several of the turns laser welded 99 or joined together to thereby provided a more secure and stronger bond between helix 40 and lead 10.

When the helix 40 is electrically inactive as in FIGS. 1, 2 and 3b, the distal end of the lead additionally has an electrode 45, electrically and mechanically coupled to an inner spring coil by a platinum alloy crimp tube. A flexible, insulating sheath 65 surrounds the inner spring coil and crimp tube. A suitable material for the insulating sheath 65 is silicone rubber. When the helix 40 is electrically inactive, it serves only as a means of securing and maintaining the electrode in firm engagement with the endocardial tissue. The helix then forms no part of the electrode structure. The helix 40 can be affixed as follows. The helix may be molded in place with silicone elastomer, as described below. A crimp or laser weld is provided at the distal end to attach the electrode to the inner spring coil.

To create an electrically active helix electrode 46 as in FIG. 3a, the crimp or laser weld would connect the helix electrode 46 to the inner spring coil 15. The electrically inactive helix 40 and helix electrode 46 can both be made of a biocompatible metal, such as platinum, MP35N alloy, or elgiloy.

Outer tubing 20 is formed of an electrically insulating material, and preferably a silicone rubber, such as clean room grade Silastic available from Dow Corning Corporation or a polyether urethane, such as Pellethane® CPR® 2363-80AE available from the Upjohn Company. These materials are additionally suitable because they are inert and well tolerated by body tissue. In any of the disclosed embodiments the distal end of the lead body should be more flexible than the proximal end of the lead body to prevent undue stress on the myocardium, as is well understood in the art. This region will generally be more flexible because only the inner spring coil 15 is present, the outer spring coil 20 having ended at the anode ring 50. Further flexibility can be accomplished by either decreasing the thickness of the TR spacer 55 wall or using more flexible material at the distal end of the outer tubing 20 than at the proximal end of the outer tubing. Furthermore, in the FIG. 3 internal torque indicator embodiment, the size of cavity 75 can be adjusted. The greater the cavity 75, the greater the flexibility.

The TR (Tip to Ring) spacer 55 lies between the anode ring 50 and the helix 40 in FIG. 2 or between the anode ring 50 and the helix electrode 46 in FIG. 3. It is made of insulating material such as silicone. It electrically insulates the inner spring coil 15 from the tissue.

The anode ring 50 is electrically active and completes the electrical circuit. It is typically formed of a polished platinum alloy with an exposed surface area much larger than that of the electrode 45 in FIG. 2 or helix electrode 46 in FIG. 3.

Sealing rings 95 and 90 as in FIGS. 2 and 3b both serve to prevent entry of body fluids into the lead assembly and prevent electrically shorting by a conductive fluid. They also mechanically stabilize the lead within the pacemaker connector block. The proximal end of the lead body is the same for both the FIG. 2 external torque indicator embodiment as for the FIG. 3 internal torque indicator embodiment. Sealing rings can be affixed with a variety of methods, one of which follows. The first sealing ring 95 lies over the top of a crimp tube to which the inner spring coil 15 is connected. The inner spring coil 15 is also connected to the pin 60. The first sealing ring 95 prevents shorting by a conductive fluid path from the pin 60 to the connector ring 70. The second sealing ring 90 lies over the top of a crimp tube to which the outer spring coil 16 is connected. The second sealing ring prevents shorting by preventing a fluid path between the body tissue and the connector ring 70.

As seen in FIG. 3b the present invention may further be incorporated within a lead having a monolithic controlled release device (MCRD) 545, preferably constructed from silicone rubber, which may be used to elute an anti-inflammatory agent. The anti-inflammatory agent, preferably a derivative of dexamethasone, such as the steroid dexamethasone sodium phosphate, is loaded in MCRD 545. The steroid also is deposited within the pores of porous electrode material 45 by application of a solution of dexamethasone sodium phosphate dissolved in a mixture of isopropanol and distilled or deionized water.

Electrode material 45 used in the lead shown in FIG. 3b is preferably a porous platinum composition coated with platinum black. The porosity, together with the platinum black coating is intended to reduce source impedance and polarization. Although platinum is the preferred material for electrode material 45, it may additionally include or be made entirely from various other materials, including but not limited to such materials as palladium, titanium, tantalum, rhodium, iridium, carbon, vitreous carbon and alloys, oxides and nitrides of such metals or other conductive materials. Of course, some materials are incompatible with others and may not be effectively used together. The limitations of specific materials for use with others is well known in the art. Examples of acceptable electrode materials and associated fabrication techniques employed to achieve the microporous structure may be found in Stokes, U.S. Pat. No. 4,506,680 and related Medtronic U.S. Pat. Nos. 4,577,642; 4,606,118 and 4,711,251 and in the Richter et al., U.S. Pat. No. 4,773,433; Heil Jr. et al., U.S. Pat. No. 4,819,661; Thoren et al., U.S. Pat. No. 4,149,542; Robblee, U.S. Pat. No. 4,677,989; Heil Jr. et al., U.S. Pat. No. 4,819,662; Mund et al., U.S. Pat. No. 4,603,704; Skalsky et al., U.S. Pat. No. 4,784,161; Szilagyi, U.S. Pat. No. 4,784,160, each of which is herein incorporated by reference.

METHOD OF MANUFACTURING A MEDICAL ELECTRICAL LEAD HAVING A TORQUE INDICATOR

The present invention also relates to a method for manufacturing a medical electrical lead having a torque indicator. The preferred embodiment of this method utilizes a cold transfer molding process and is used to manufacture a lead as depicted in FIG. 3b.

Figure 4:
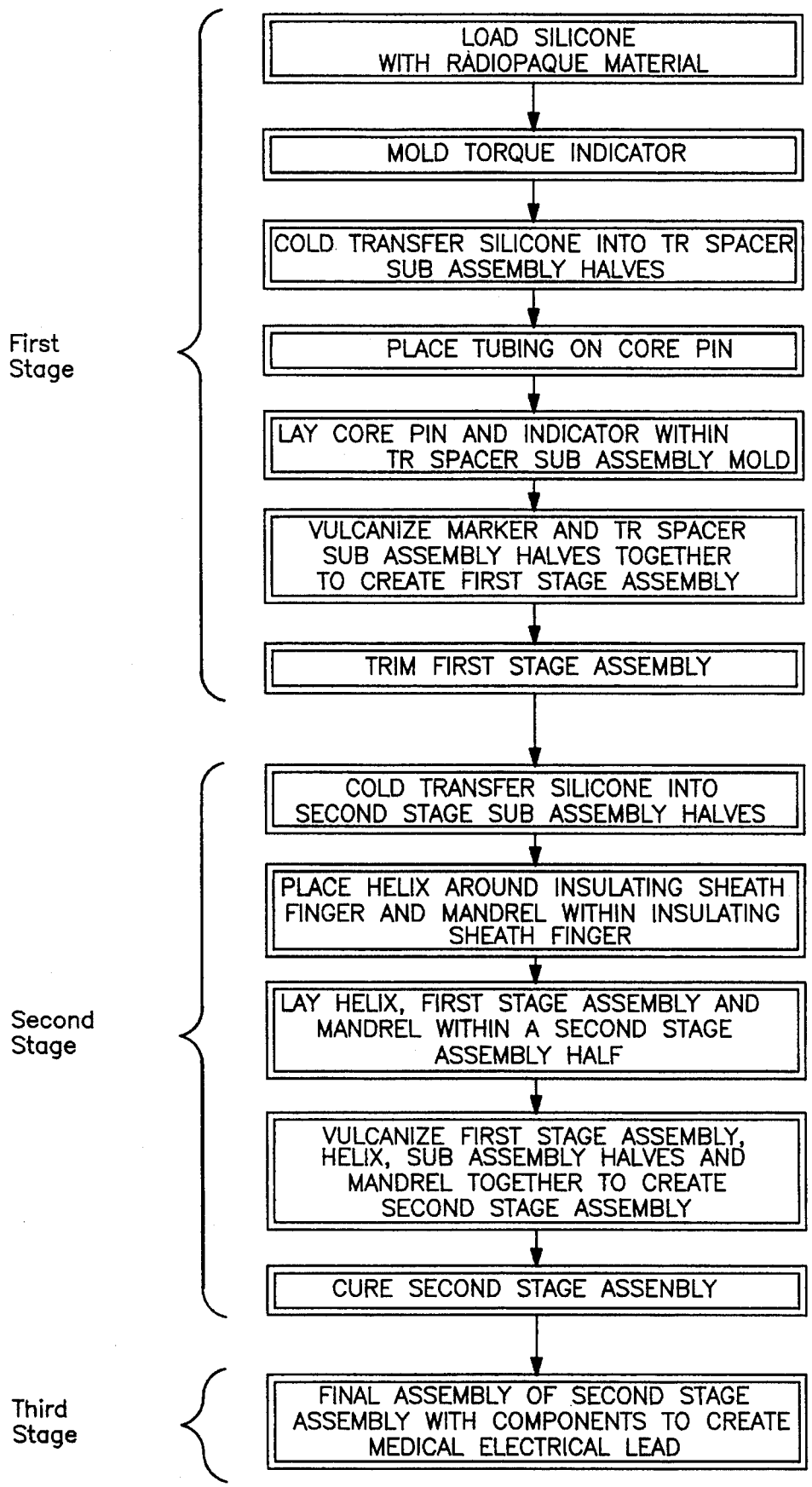
FIG. 4 shows a flow chart of a first method of manufacturing a lead having a torque indicator.

A flowchart representing the salient steps of this method of manufacturing a medical electrical lead having a torque indicator is shown in FIG. 4. As seen, the method of manufacturing consists essentially of three stages: The first stage involves forming the torque indicator and mounting the indicator with a TR spacer sub assembly 56 to form what is called the first stage assembly; the second stage involves molding the helix and the first stage assembly together to form what is called the second stage assembly or the TR spacer 55; and the third and final stage involves assembling the TR spacer 55 with the various components to create a medical electrical lead 10.

Stage one utilizes a cold transfer molding process and has essentially seven steps. These steps are depicted in detail in FIG. 4 and illustrated in FIGS. 5–12. The first two steps relate to the formation of the torque indicator or marker 36. As discussed above preferably torque indicator 36 comprises a radiopaque marker to thereby provide torque indication through use of a fluoroscope. It should be realized, however, that the present invention concerns the general provision of any torque indicator which may provide torque indication through any means, including visible or conventional illumination, as well as through other means, such as ultrasound.

Formation of the preferred radiopaque torque indicator or marker 36 is accomplished by "loading" or mixing silicone with a radiopaque material to form a composite dispersion. The preferred silicone is the model 1511 medical adhesive available from Rehau A. G. located in Rehau, Federal Republic of Germany. Although in the preferred embodiment silicone is used, other room-temperature vulcanization adhesives may also be used, such as other various silicones or polyurethanes.

The radiopaque material is preferably spheres of platinum having a size of 25–32 μm. Acceptable spheres are available from Johnson Matthey, Inc. located in West Chester, Pa. Although in the preferred embodiment spheres are used, other shapes and configurations of platinum may be used, such a fines, for example. Moreover, although in the preferred embodiment platinum is used, other radiopaque, bio-compatible materials may also be used, such as gold, iridium or tantalum for example.

Once the dispersion is created it is introduced into a suitably shaped mold, preferably cylindrical, and cured to form torque indicator or marker 36. The mold is preferably made from DELRIN™ (acetal homopolymer) available from DuPont located in Wilmington, Del., although other hydroscopic materials may be used. Curing is accomplished by heating the torque indicator 36 for 5 hours at 70 degrees celsius. It should be noted, however, that because a room-temperature vulcanization adhesive is used, vulcanization per se is not necessary for the material used in torque indicator 36 to solidify. Thus solidification may alternatively be accomplished by allowing the indicator 36 to stand at approximately 22 degrees celsius (room temperature) for 24 hours.

Figure 5:
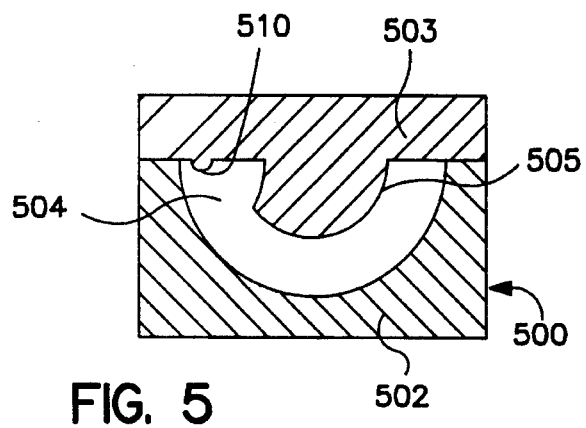
FIGS. 5–9 show cross sectional views of the molding process used in the first method of manufacturing a lead having a torque indicator.
Figure 6:
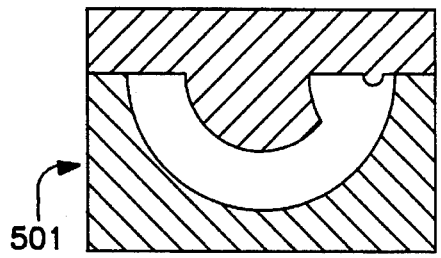
Figure 10:
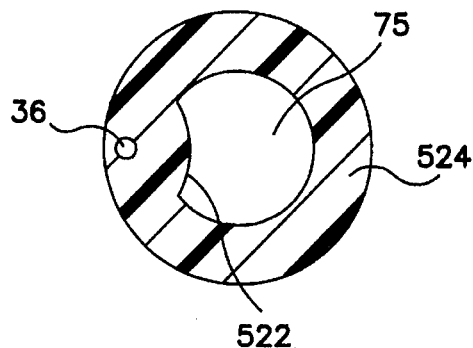
FIG. 10 shows a cross sectional view of a first stage sub assembly.

Next indicator 36 is incorporated into TR spacer 55. This requires several steps. First a TR spacer sub assembly 56 is formed. This is accomplished by first forming complementary halves using molds 500, 501 seen in FIGS. 5 and 6 using a cold transfer molding method. Because the molds 500, 501 are complementary only one need be discussed in detail. As seen in FIG. 5 mold 500 consists of a bottom half 502 and a top plate 503. Halves 502, 503 mate together to define mold cavity 504 therebetween. Mold cavity 504 is shaped to conform to one half of the TR spacer sub assembly 56. Top plate 503 has a descending member 505 which defines cavity 75 (as best seen in FIG. 10) and nose 510 which defines groove 511 within wall of TR spacer 55. The grooves 511 of each complementary half of the TR spacer sub assembly 56 mate together and are used to mount torque indicator 36 within TR spacer 55. Specifically the torque indicator 36 is fit within groove 511 of one half of the TR spacer, as best seen in FIG. 7.

Formation of TR spacer 55 using these molds and a indicator 36 is accomplished as follows. First the respective halves 507, 508 of TR spacer sub assembly 56 are formed using molds seen in FIGS. 5 and 6, and specifically by first filling or cold transferring silicone into mold cavity 504 under a pressure of 6 tons for 15 seconds. Silicone is transferred through a transfer port not shown in the present FIGS. Although also not shown in the FIGS. molds 500, 501 may additionally feature a flash groove, or spillover area, into which excess or overflow silicone from mold cavity 504 may flow. Next top plate 503 is removed and marker 36 is fit within groove 511 of half 508.

Figure 11:
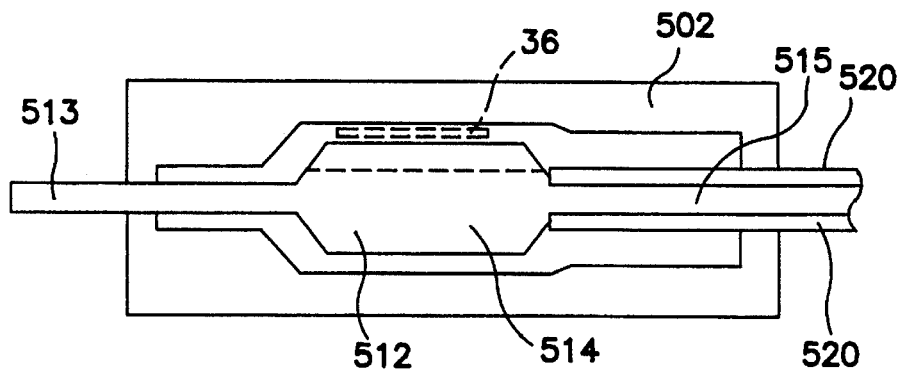
FIG. 11 shows the TR spacer sub assembly as it is molded.

Next core pin 512 is prepared. Core pin 512 is used to retain the shape of cavity 75 within TR spacer 55 during vulcanization, as described below. Core pin 512 has three sections: distal finger 513, cavity section 514 and insulating sheath finger 515. As best seen in FIG. 11 insulating sheath finger 515 of core pin has a section of a tubular insulating sheath 65 inserted over. This permits TR spacer sub assembly 56 to be molded having a length of tubular insulating sheath 65 integral therewith. In the bipolar embodiment of the present invention tubular insulating sheath 65 will act as the inner insulator in the final lead.

Figure 7:
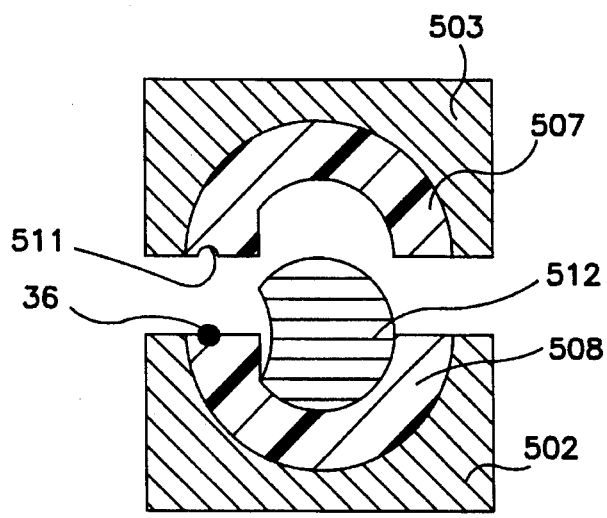
Figure 8:
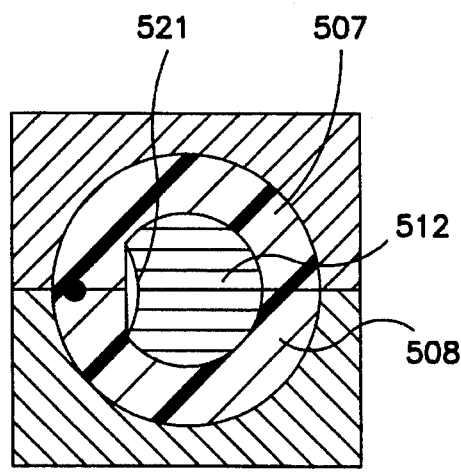

With tubular insulating sheath 65 fitted over insulating sheath finger 515 of core pin 512, core pin 512 is next fit within one half of cavity 75 of half 508 and a complementary half 507 of the TR spacer sub assembly 56 is mated therewith, as best seen in FIGS. 7 and 8. As seen core pin 512 is shaped having a cutout area 521.

Figure 9:
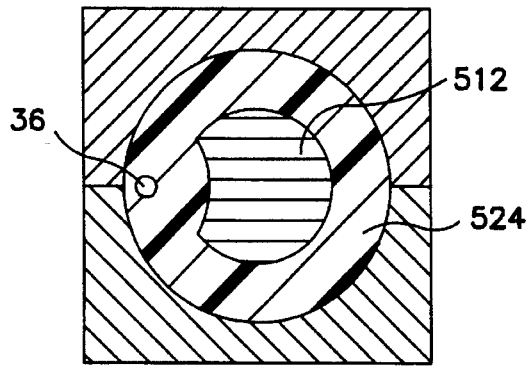

With the core pin 512 in place and the molds fitted together as shown in FIG. 8 the assembly is vulcanized. Vulcanization is accomplished by heating the assembly at 260 degrees Fahrenheit for 7 minutes at 3 tons pressure. As best seen in FIG. 10, during vulcanization the silicone material flows somewhat and cutout area 521 permits silicone, or whatever other material is used, to flow somewhat and thereby create a reinforced section 522 directly proximate to marker 36 as best seen in FIG. 9. As seen cavity 75 is formed which is preferably not symmetrical as a thickened silicone area should be formed under the torque indicator 36 for strengthening so as to provide a secure and reliable mounting of torque indicator 36. Although it is important for torque indicator 36 to be reliably mounted, overall distal end of lead should be flexible. This quality is achieved through the provision of cavity 75. Cavity 75 contributes to the flexibility of the distal end of the lead 10. The greater the cavity 75, the greater the flexibility.

It should be noted that the additional material required for the flow depicted by the arrows in FIG. 9 is provided for by the dimensions of halves 507, 508 and the diameter of core pin 512. Specifically halves 507, 508 are formed to be thicker than required, that is they have an smaller inner diameter than is required to form cavity 75. Core pin 512 conforms in diameter, however, to cavity 75. Thus during the vulcanization of halves 507, 508 with core pin 512 therein, the walls of halves 507, 508 are forced to be thinned somewhat. That it is believed that it is the excess material from the walls of halves 507, 508 which flows to create reinforced section 522.

Figure 12:
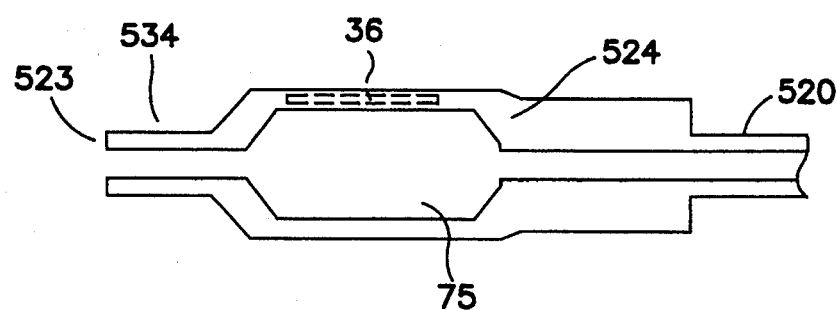
FIG. 12 shows the first stage assembly.

Once vulcanization is complete, core pin 512 is removed. Core pin 512 is removed by simply withdrawing it through distal end 523, as shown in FIG. 12. Because silicone is readily flexible, distal end 523 will expand to accommodate this withdrawal. It is also possible, if necessary, to chemically expand first stage assembly before removing core pin 512. Chemical expansion may be accomplished by soaking the first stage assembly 524 and core pin 512 in 100% heptane for 30 seconds. It has been found by the inventors that chemically expanding first stage assembly 524 prior to removing core pin 512 is preferred because it reduces the likelihood of tearing on distal end 523. Next, excess silicone, if any, is trimmed away. With the core pin 512 removed and any excess silicone trimmed the first stage is complete. As seen in FIGS. 10 and 12, at the end of first stage the first stage assembly 524 of TR spacer sub assembly 56 has marker 36 and tubular insulating sheath 65 integral therewith.

Figure 13:
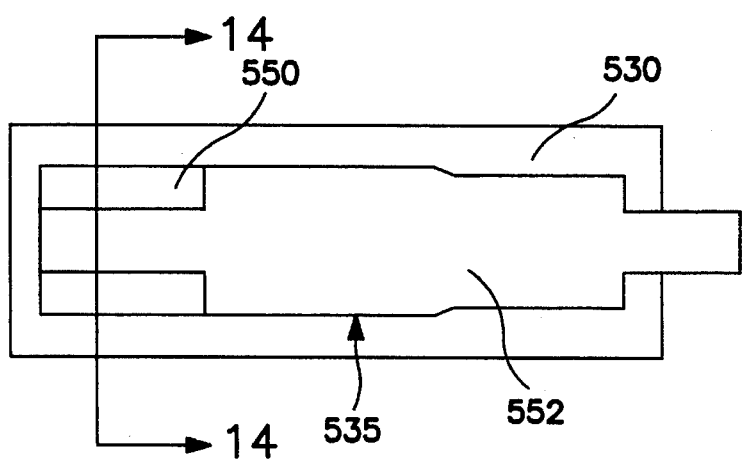
FIG. 13 shows a second stage sub assembly as it is molded.
Figure 14:
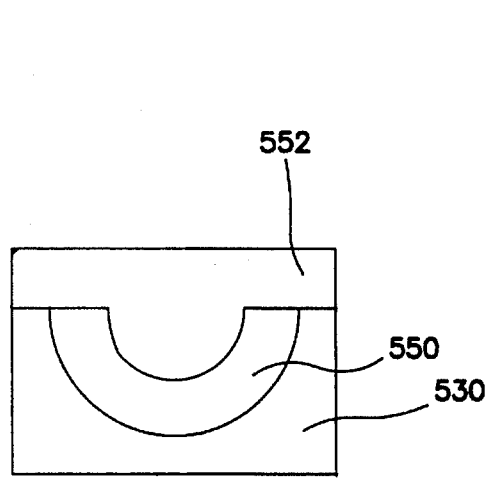
FIG. 14 shows a cross sectional view of a second stage sub assembly half as it is molded.
Figure 16:
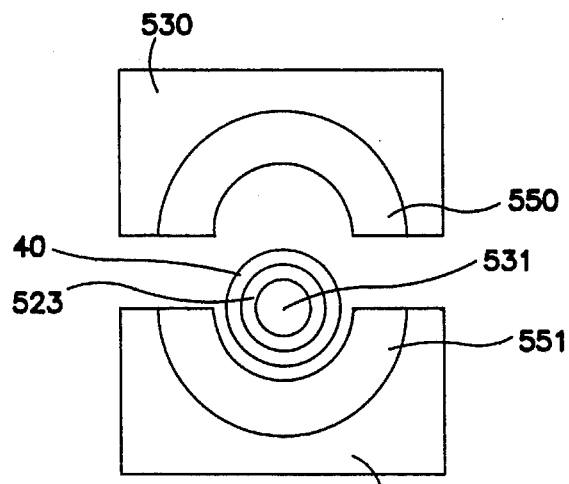
FIG. 16 shows a cross sectional view of the second stage assembly as the helix, mandrel, first stage assembly and second stage sub assembly halves are brought together and vulcanized to create the second stage assembly.

The second stage of the cold transfer molding process is next. This consists of completing the assembly of TR spacer 55, viz. attaching helix 40 to the first stage assembly 524. Attachment is accomplished through a second set of molds 530 and a mandrel 531 as depicted in FIGS. 13–17. The first step in the second stage consists of cold transferring silicone into a pair of second molds 530 to create second stage sub assembly half 550, as depicted in FIGS. 13 and 14. Although only a single second stage sub assembly half 550 is depicted in FIGS. 13 and 14 it should be understood that two second stage sub assembly halves 550 are formed, as depicted in FIG. 16. Because these halves 550 are symmetrical, however, only one need be discussed in any detail. As seen in FIGS. 13 and 14 second stage sub assembly half 550 is formed by cold transferring silicone into second stage mold 530. Second stage mold 530 has a second stage mold cavity 535 which corresponds to second stage assembly 540. To form second stage sub assembly half 550, however, only a portion of second stage mold cavity 535 is filled, and to accomplish this force plate dam 552 is inserted therein. Cold transfer of silicone is accomplished by pressurizing the silicone to four tons for between five and 10 seconds so it flows into mold cavity 535. As seen in FIG. 13 14 force plate dam 552 block a substantial portion of second stage mold cavity 535 from silicone and causes second stage sub assembly half 550 to be a half cylinder in shape. Once a pair of second stage sub assembly halves 550 are formed, force plate dam 552 is removed from mold cavity 535.

Figure 15:
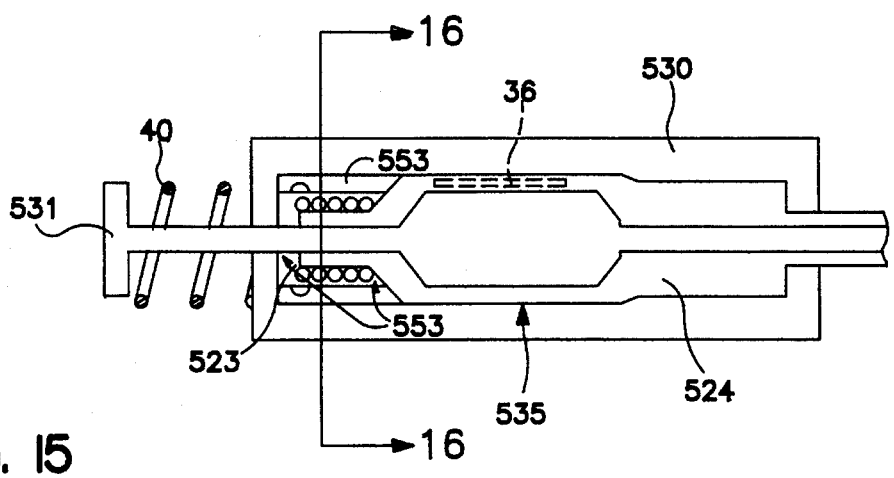
FIG. 15 shows the second stage assembly as the helix, mandrel, first stage assembly and second stage sub assembly halves are vulcanized together to create the second stage assembly.
Figure 17:
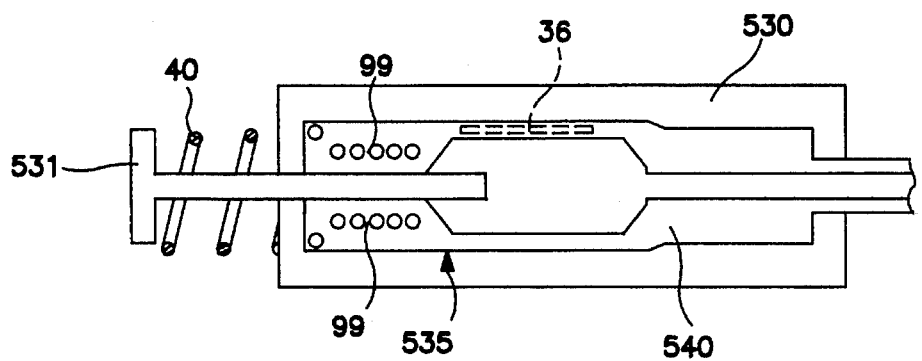
FIG. 17 shows the second stage assembly as it is vulcanized.

Next and first stage assembly 524 is prepared for attachment of the helix 40. Helix 40 is placed around insulating sheath finger 515 and mandrel 531 is in insulating sheath finger 515. Next this assembly is placed within a second stage mold cavity 535 having a second stage sub assembly half 550, as seen in FIGS. 15 and 16. Then a second half of mold 530 having a corresponding second stage sub assembly half 550 is mated therewith, as best seen in FIG. 16. Once mated together, helix 45 is fit between second stage sub assembly half 550 and insulating sheath finger 515, as best seen in FIG. 15.

Next first stage assembly 524, helix 45, second stage sub assembly halves 550 and mandrel 531 are vulcanized. Vulcanization is preferably accomplished by heating the mold to 260 degrees Fahrenheit for seven minutes at three tons pressure to create the second stage assembly 540. As seen in a comparison of FIGS. 15 and 17, vulcanization essentially causes the first stage assembly 524 and second stage sub assembly halves 550 to join together and anchor helix 45 therewith. Specifically during vulcanization silicone will flow between first stage assembly 524 and second stage sub assembly halves 550 as depicted by arrows 553 in FIG. 15.

Figure 18:
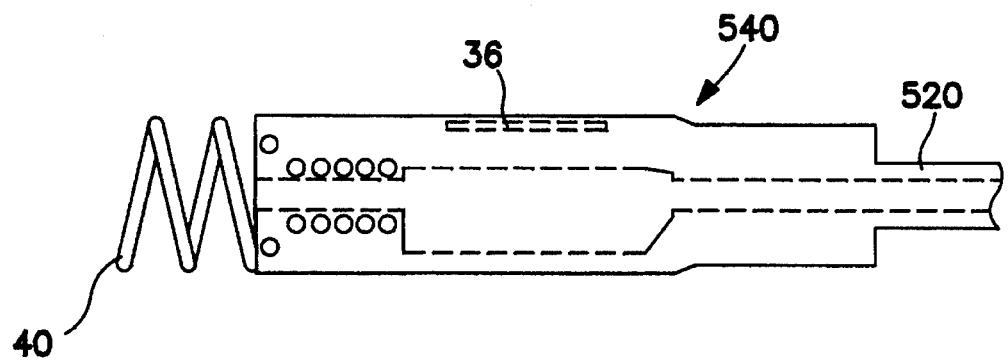
FIG. 18 shows the second stage assembly after it has been vulcanized and the mandrel removed.

Once vulcanized, second stage assembly 540 is removed from mold 530. Mandrel 531 is removed from within insulating sheath finger 515 and second stage assembly 540 is cured. Curing is accomplished by heating second stage assembly 540 at 325 degrees Fahrenheit for fifteen hours. Once cured second stage assembly 540 is cooled and trimmed, if necessary. As seen in FIG. 18 second stage assembly 540 has helix 40, indicator or marker 36, and tubular insulating sheath 65 integral therewith.

The final stage consists of assembling the lead 10. Basically this step consists of inserting an inner conductor 15 through tubular insulating sheath 65 and electrode 45 to the distal end. Electrode 45 and inner conductor 15 are electrically connected. Next a ring electrode 50 is attached to TR spacer 55 and an outer conductor 16 is electrically attached thereto. Next an outer insulator 20 is place over outer conductor 16. Finally a connector pin 70 is attached to proximal end of lead 10.

Figure 19:
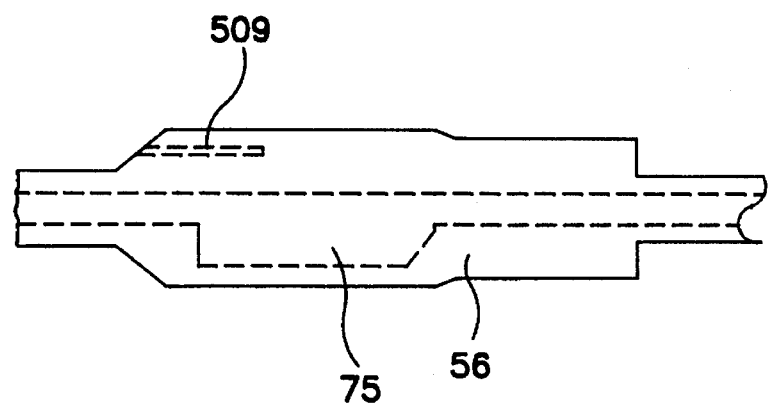
FIG. 19 shows the first stage assembly having a side hollow molded therein and ready to be backfilled with a radiopaque material.

A second method for manufacturing a medical electrical lead having a torque indicator is depicted in FIG. 19. This method consists essentially of backfilling a hollow 509 with a radiopaque material. Specifically TR spacer sub assembly 56 is molded so as to have a side hollow 509 formed therewith as depicted in FIG. 19. Such a TR spacer sub assembly 56 may be molded using molds similar to those shown above. In the alternative it is also possible to mold the TR spacer sub assembly 56 as a single piece having hollow 509 formed therewith. Such a molding may be accomplished with a mold having a outstanding finger shaped to form hollow 509. In the alternative hollow 509 may further be formed through provision of a second core pin. Specifically once halves 507, 508 are produced having an additional groove corresponding to hollow 509, halves 507, 508 are mated together as described above using a core pin to maintain cavity 75. In addition during this step an additional core pin should be used to maintain hollow 509. Once halves 507, 508 were joined therewith and hollow 509 created thereby.

Next a composite dispersion of silicone and a radiopaque material is formed as discussed above. The side hollow 509 is then backfilled or injected with the composite dispersion. In such a manner first stage TR spacer assembly 56 is created having a torque indicator 36 therewith. Once first stage TR spacer sub assembly 56 is trimmed, vulcanized and completed, it is then assembled into a lead 10 as discussed above, and specifically according to the second and third stages shown in FIG. 4.

Figure 2B:
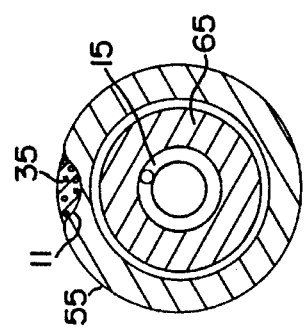
FIG. 2b shows a view of a cross-section of an alternate embodiment of a lead having an external torque indicator positioned within a furrow.

The third method of manufacturing a torque indicator includes applying an uncured platinum loaded adhesive directly to the outside of the TR spacer 55. Such a lead 10 can be seen in FIG. 2. Basically this method consists of creating a platinum loaded adhesive. The preferable adhesive is Rehau medical adhesive 1511, as discussed above. The preferable platinum used is spherical, as discussed above, although other radiopaque materials besides platinum may also be used, also as discussed above. Next the platinum loaded adhesive is applied to the exterior of the TR spacer 55, preferably in a straight line. The adhesive bonds to the exterior of TR spacer 55. Next the TR spacer 55 may then be assembled into a lead 10, as described above. In this fashion a lead 10 is formed which, as the distal end of TR spacer 55 begins to bend due to torque the indicator or marker 36 will also and thereby indicate torque. Of course, it is also quite conceivable to only apply the platinum loaded adhesive to TR spacer 55 once all the components have been assembled into a lead 10. In addition TR spacer 55 may additionally be provided with a furrow 11, as best seen in the cross sectional view of FIG. 2b. Provision of furrow produces a TR spacer having a smoother exterior surface, as best seen in a comparison of FIGS. 2a and 2b. Furrow 11, of course, may be produced using the molding process described above through a correspondingly shaped mold.

It must be understood that the above methods are described specifically in the context of manufacturing a bipolar lead, although they may also be used to manufacture a unipolar lead.

It must also be understood that the above methods, and specifically the times and temperatures used, may require some variance to achieve consistently satisfactory results due to the specific characteristics of the materials chosen, the thermal characteristics of the molds used as well as the particular geometries and dimensions of the parts formed.

Those skilled in the art will recognize that there are other methods of manufacturing a radiopaque marker. Radiopaque foils, radiopaque coils or silicone elastomer with platinum milled in could be used. Moreover as discussed above, those skilled in the art will realize that the present invention is not limited to only the provision of a radiopaque marker, but rather relates generally to the provision of a torque indicator incorporated on or into a lead to thereby indicate rotation and torque, either through conventional illumination, ultrasound or fluoroscopy.

The preceding specific embodiments and methods are illustrative of the practice of the invention. It is to be understood, however, that other expedients known to those skilled in the art or disclosed herein, may be employed without departing from the spirit of the invention or the scope of the appended claims, including substituting elements or components which perform substantially the same function in substantially the same way to achieve substantially the same result for those described herein.

LIST OF PARTS

| No. | Component |
| --- | --- |
| 10 | Lead |
| 15 | Inner Spring Coil |
| 20 | Outer Tubing |
| 25 | Stylet |
| 35 | External Torque Indicator |
| 36 | Internal Torque Indicator |
| 40 | Electrically Inactive Helix |
| 45 | Electrode |
| 46 | Helix Electrode |
| 50 | Anode Ring |
| 55 | TR Spacer |
| 56 | TR spacer sub assembly |
| 60 | Pin |
| 65 | Insulating Sheath |
| 70 | Connector Ring |
| 75 | Cavity |
| 80 | Tip |
| 85 | Crimp Tube |
| 90 | Second Sealing Ring |
| 95 | First Sealing Ring |
| 135 | External Torque Indicator |
| 140 | Electrically Inactive Helix |
| 200 | Heart |
| 205 | Right Ventricle |
| 210 | Right Atrium |
| 215 | Left Atrium |
| 220 | Left Ventricle |
| 225 | Superior Vena Cava |
| 230 | Tricuspid Valve |
| furrow | 11 |
| molds | 500, 501 |
| bottom half | 502 |
| top plate | 503 |
| mold cavity | 504 |
| descending member | 505 |
| hollow | 509 |
| nose | 510 |
| groove | 511 |
| core pin | 512 |
| distal finger | 513 |
| cavity section | 514 |
| insulating sheath finger | 515 |
| cutout area | 521 |
| reinforced section | 522 |
| distal end | 523 |
| first stage assembly | 524 |
| molds | 530 |
| mandrel | 531 |
| injection port | 532 |
| hollow | 533 |
| sleeve | 534 |
| second stage mold cavity | 535 |
| second stage assembly | 540 |
| monolithic controlled release device (MCRD) | 545 |
| second stage sub assembly half | 550 |
| force plate dam | 552 |
| arrows | 553 |

What is claimed is:

1. A method of manufacturing a medical electrical lead having a torque indicator comprising:

loading a first material into a polymer to form a composite dispersion;

forming a first part having a hollow in a side wall;

introducing said composite dispersion into said hollow in said side wall to form a first stage assembly; and assembling said first stage assembly into a medical electrical lead.

2. The method according to claim 1 wherein said step of assembling said first stage assembly into a medical electrical lead comprises:

mounting a biocompatible insulator having a central lumen to said first stage assembly;

positioning a conductor coil through said central lumen;

coupling an electrode to a distal end of said conductor coil; and coupling a connector pin to a proximal end of said conductor coil.

3. The method according to claim 1 further comprising the steps of curing said composite dispersion at a temperature of 70 degrees celsius for 5 hours and vulcanizing said first stage assembly at a temperature 260 degrees Fahrenheit for 7 minutes at 3 tons pressure.

4. A method of manufacturing a body-implantable lead comprising:

molding a radiopaque mixture into a first shape in a first mold;

removing said first shape from said first mold;

providing said first shape in a second mold; and providing a biocompatible insulator in said second mold to mold a lead body having a central lumen and an outer wall, said outer wall having said first shape attached therewith.

5. The method of claim 4 wherein the step of molding a radiopaque mixture into a first shape in a first mold further comprises the step of loading a polymer with a radiopaque material.

6. The method of claim 5 wherein said radiopaque material are spheres of platinum having a size of between 25–32 µm.

7. The method of claim 5 wherein said polymer is a room-temperature vulcanization adhesive.

8. The method of claim 5 wherein said polymer is silicone.

9. The method of claim 5 wherein the step of providing a biocompatible insulator in said second mold to mold a lead body having said first shape therewith further comprises the step of providing a silicone mixture.

10. The method of claim 4 wherein the step of providing a biocompatible insulator in said second mold to mold a lead body having a central lumen and an outer wall, said outer wall having said first shape therewith further comprises the step of providing a non-symmetrical central lumen in a distal portion of said lead body.

11. A method of manufacturing a body-implantable lead comprising:

forming a lead body having a center lumen;

loading an adhesive mixture with a radiopaque material to create a radiopaque loaded adhesive; and applying said radiopaque loaded adhesive to said lead body at a position offset from a center axis of said lead body.

12. The method of claim 11 wherein said step of applying said radiopaque loaded adhesive to said lead body at a position offset from a center axis of said lead body is done on an exterior surface of said lead body.

13. A method of manufacturing a body-implantable lead comprising:

forming a lead body having a central lumen and an outer wall, said lead body further having a non-coaxial lumen in said outer wall, said lead body further having a proximal end and a distal end;

providing a radiopaque mixture in said non-coaxial lumen in said outer wall;

providing a conductor within said central lumen of said lead body, said conductor running from said proximal end of said lead body to said distal end of said lead body;

coupling a conductor pin to a proximal end of said lead body and to said conductor; and coupling an electrode to said distal end of said lead body and to said conductor.

14. The method of claim 13 further comprising the step of forming said radiopaque mixture by the step of mixing a polymer and a radiopaque material.

15. A method of manufacturing a body-implantable lead comprising:

forming a radiopaque marker into a first shape;

forming a first half of a lead body distal end;

forming a second half of a lead body distal end;

joining said first half, said second half and said radiopaque marker together to form a lead body distal end;

mounting a biocompatible insulator having a central lumen to said lead body distal end;

positioning a conductor coil through said central lumen;

coupling an electrode to a distal end of said conductor coil; and coupling a connector pin to a proximal end of said conductor coil.

16. The method according to claim 15 wherein the step of forming a radiopaque marker comprises loading a polymer with a radiopaque material.

17. The method according to claim 15 wherein the step of forming a radiopaque marker comprises forming a radiopaque foil into a first shape to create a radiopaque marker.

18. The method according to claim 15 wherein the step of forming a radiopaque marker comprises forming a radiopaque coil into a first shape to create a radiopaque marker.

\* \* \* \* \*